United States Patent [19] [11] 3,997,656
Wertlake et al. [45] * Dec. 14, 1976

[54] TISSUE STAINING METHOD AND COMPOSITION

[75] Inventors: Paul T. Wertlake, Los Angeles, Calif.; James S. Harrison, Ringwood, N.J.

[73] Assignee: Applied Bioscience, Fairfield, N.J.

[ * ] Notice: The portion of the term of this patent subsequent to Jan. 21, 1992, has been disclaimed.

[22] Filed: July 15, 1975

[21] Appl. No.: 596,010

Related U.S. Application Data

[63] Continuation-in-part of Ser. No. 373,276, June 25, 1973, abandoned, which is a continuation-in-part of Ser. No. 338,732, March 7, 1973, Pat. No. 3,862,300.

[52] U.S. Cl. .......................................... 424/3; 8/10; 8/94.1 R; 8/94.11; 8/94.33; 424/75
[51] Int. Cl.² ..... A01N 1/02; G01N 1/00 G01N/1/30
[58] Field of Search ............. 424/3, 75; 8/10, 94.1, 8/94.11, 94.33

[56] References Cited
UNITED STATES PATENTS

| 3,057,775 | 10/1962 | Rendon | 424/3 X |
|---|---|---|---|
| 3,257,279 | 6/1966 | Schain | 424/3 |
| 3,389,052 | 6/1968 | Ehrenreich | 424/3 |
| 3,862,300 | 1/1975 | Wertlake | 424/3 |

OTHER PUBLICATIONS

Bowling, Histopath. Lab. Proceedures of the Path Anat. Br. of the Nat. Cancer Inst. NIH., Bethesda, Md., pp. 17, 18, 24, 25, 28 (P.H.S. Pub. No. 1595, 1967).

Primary Examiner—Albert T. Meyers
Assistant Examiner—A. P. Fagelson

[57] ABSTRACT

A superior and extremely rapid histological staining method is described in which frozen tissue is briefly immersed in an aqueous solution comprising trichloroacetic acid, zinc chloride and formaldehyde and then in a second solution comprising hematoxylin. The tissue can be further counterstained if desired. Also disclosed are improved fixatives useful in this and other histological techniques.

21 Claims, No Drawings

TISSUE STAINING METHOD AND COMPOSITION

CROSS-REFERENCE

This is a continuation-in-part of Ser. No. 373,276, filed June 25, 1973, now abandoned, which in turn is a continuation-in-part of Ser. No. 338,732, filed Mar. 7, 1973, now U.S. Pat. No. 3,862,300 issued Jan. 21, 1975.

DETAILED DESCRIPTION

The present invention pertains to a superior histological fixative for use in preparing tissue specimens for microscopic and histological examination. The present invention also pertains to a histological staining method for tissue specimens prefatory to microscopic examination.

Various methods of fixation have heretofore been employed by the art, the precise technique of which depends upon the particular investigation being conducted. Freezing the tissue or embedding it in wax is often sufficient but materials are liable to be lost, altered or moved within the tissues. Various improvements such as freeze-drying utilizing a vacuum or the substitution of ice in the frozen cell by alcohol have been used to avoid these difficulties but are often cumbersome on a large scale. Utilization of chemical fixation techniques can be employed in certain instances but these generally lack wide applicability for different tissues and procedures.

In a first embodiment therefore the present invention pertains to a novel histological fixative comprising an aqueous solution of trichloroacetic acid, zinc chloride, and formaldehyde. This fixative causes minimal damage to the tissue cells, is convenient in actual use, and can be employed in a wide variety of tissue types.

In a second embodiment, the present invention pertains to a histological staining method in which the novel fixative is employed.

The selective staining of tissue cells, both to identify various parts of the cell and to distinguish different types of cells, is a well known diagnostic technique. Suitable techniques yielding reproducible results are however often time-consuming and cumbersome. In typical cryogenic applications, two major techniques are followed: the tissue is rapidly frozen, sectioned in part, fixed in, for example, formaldehyde or alcohol, stained, most frequently with a single stain, coverslipped and examined. This preparation is not permanent and has a limited life of only several hours. While it permits a more or less rapid examination of the tissue, the technique has several disadvantages, most notably the different appearance, principally tinctorial, of the specimen from the usual microscopic preparations. This result increases the difficulty of obtaining a correct interpretation, so that in order to have a more definitive microscopic analysis, as well as a permanent preparation of the original tissue, a second technique is followed. In this approach, the frozen tissue is thawed, fixed, dehydrated, infiltrated with organic solvents, embedded in paraffin and sectioned. These sections are in turn deparaffinized, hydrated, stained, dehydrated and coverslipped. This provides a permanent microscopic preparation of the material originally studied in the temporary cryogenic method but as noted, the technique is extremely lengthy and cumbersome and the specimens are not exact replicas of the original tissue. In addition to the possible damage caused by ice crystal formation and thawing, the specimen may assume different orientation leading to a different plant of sectioning. Tissue is also lost in the course of the chemical and physical processing.

The interplay of these two techniques, and their inherent disadvantages, can be most vividly seen in, for example, the case of a suspected malignancy. Typically, a tissue sample removed from a patient in the course of exploratory surgery will be subjected to the first technique in order to permit the surgeon to make an immediate decision concerning the nature and extent of radical surgery. Preparation of a permanent microscopic specimen to permit confirmation of the diagnosis can require as much as twenty-four hours, or more, which obviously limits the microscopic examination of tissues removed during surgery to the more rapid but less definitive temporary preparations since the patient cannot be maintained in the operating room for the longer period required for a permanent preparation. Moreover, final results of tissue studies are not known for one or several days, thereby increasing or prolonging the natural apprehension of patient and family. Since the gross specimens upon which the diagnosis were based are often not suitable for retention, elaborate preservation steps must be taken to document the medical condition and provide a long term reference. It occasionally happens that the tissue lost in processing, although small, represents that portion of the tissue in the temporary preparation upon which the microscopic diagnosis was based.

There is described in the above recited applications Ser. No. 373,276 and Ser. No. 338,732, a novel histological fixative comprising a solution of trichloroacetic acid, zinc chloride and formaldehyde in an aqueous lower alkanol. This fixative was found to cause minimal damage to the cells of the tissue, to be convenient in actual use, and suitably employed with a wide variety of tissue types.

It has now been found that by extending the proportions of certain of the specific ingredients in the particular composition described in Ser. Nos. 338,732 and 373,276 and/or adding or eliminating other components, the range of applications for the fixative can be greatly extended. In particular, it has been found that as between the mixture of the three active ingredients, trichloroacetic acid, zinc chloride, and formaldehyde, the relative proportions can vary considerably. For example, the trichloroacetic acid can constitute from about 5% to about 85%, by weight, of the mixture, the zinc chloride can constitute from about 4% to about 30%, by weight, and the formaldehyde can constitute from about 3% to about 70%, by weight (calculated as 100% formaldehyde). These three components can thus be selected in amounts such that their combined individual percentage compositions total 100% of the mixture. As will be seen hereafter, such variations are desirable in obtaining fixative compositions suitable for specific applications and/or specific tissues.

Moreover, it has been found that the solvent system of aqueous alkanol also can be varied so as to extend the range of applicability. Thus while for some applications it is desirable to increase the ratio of alkanol to water, in others, the alkanol can be reduced and indeed eliminated altogether.

It has also been found that the concentration of the mixture in the solvent can be varied, from as low as about 1% to as high as about 50%, wt/vol.

Finally it has been found that certain adjuvants are advantageously added in some particular applications.

The fixative is prepared by combining the trichloroacetic acid, zinc chloride and formaldehyde in the desired proportions and then dissolving this mixture in an aqueous medium so as to provide a final solution of from about 1 to about 50% weight/volume of the mixture in the aqueous medium. In the case of the formaldehyde, it is convenient to utilize a formaldehyde solution, as for example the conventional 37% formaldehyde solution, and to make appropriate adjustments in the amount of water which is added.

Although the order of mixing the individual components is not critical, this mixing is accompanied by an exothermic reaction and some care should thus be taken in this preparation. Moreover, since a small amount of insoluble material can be observed in the final solution, it is desirable to filter the solution once the components have been mixed.

When the aqueous medium is an aqueous alkanol, the lower alkanol can be any of the well known alcohols having from one to four carbon atoms as for example methanol, ethanol, n-propanol, isopropanol, n-butanol and the various branched butanols. Methanol is highly satisfactory and preferred from the standpoint of economics and solvent power. Although the amounts referred to herein are based upon pure alkanol, it is apparent that alkanols containing various amounts of water can be employed in the formulation of the present fixative, making appropriate adjustments in the volumes of the alkanol and additional water which is added.

In some applications, it is desirable to include a surfactant in the composition. The surfactant can be any of the wellknown materials of this type, as for example the alkylaryl polyether alcohols, sulfonates or sulfates. The amount present will generally be small, usually less than 1%, vol/vol of the aqueous medium.

In other applications, it is desireable to add a water soluble wax such as a polyethylene glycol. This acts as a lubricant maintaining the flexibility of cells and also provides a protective seal reducing the effect of atmospheric oxygen on the cells.

The versatility of this fixative can be seen from the following representative compositions mersed in the fixative for a short period of time, as for example 1 or 2 hours, and then removed and processed in the usual fashion. Tissue which is so fixed provides excellent specimens upon sectioning. This is true even with such tissue as renal and brain tissue which specimens are known to be difficult to prepare.

Composition B is particularly advantageous for the preparation of bone specimens. It demonstrates significant decalcifying action, rendering the bone specimen rubbery, yet maintains nucleic proteins unimpaired and provides an excellent binding site for later staining. Unlike nitric acid, a widely used decalcifying agent, nuclear staining is not impaired upon overexposure. It is also used in the conventional manner, e.g. fixing the specimen through immersing, setting the fixed specimen in paraffin, dehydrating and staining as with hemotoxylin.

Composition C is particularly useful for cytological preparation. In such preparation, small tissue fragments such as one obtained in a microbiopsy or swab specimen of exfoliated cells are transferred directly to a microscope slide for examination. The fragments are not imbedded in a matrix nor are they sectioned. Fixing such cytological specimens has presented a problem because of the mobility of the cells, their susceptibility to alteration through exposure to air, and their resistance to satisfactory staining. The above composition can be applied over such specimens by simple brushing and not only provides excellent fixation and susceptibility to staining but also protects the specimen from deterioration, as by oxidation from atmospheric oxidation. It is significantly superior to the use of alcohol, ether-alcohol and 10% buffered formalin which heretofore have been used for fixing such cytological preparations.

It is to be appreciated that the foregoing are merely typical and not limiting. For example, compositions such as B while highly useful for bone tissue can also be used with little or no change for fixing lymph node tissue in which case, a significant clearing of fat is observed. Likewise by addition of a small amount of gluteraldehyde to Composition A with adjustment of the pH towards neutrality, a fixative which is suitable

| Ingredient | A Amt | % | B Amt | % | C Amt | % |
|---|---|---|---|---|---|---|
| $CCl_3COOH$ | 120g. | 8% | 296.5g. | 80.3% | 22.25g. | 32% |
| $ZnCl_2$ | 400g. | 25% | 20.0g. | 5.4% | 11.25g. | 16% |
| HCHO* | 1055g. | 67% | 52.7g. | 14.3% | 36.7 g. | 52% |
| Total | 1575g. | 100% | 369.2g. | 100% | 70.2 g. | 100% |
| Surfactant[1] | — | | 0.1 ml | | — | |
| Wax[2] | — | | — | | 920 ml | |
| $H_2O$* | 1.663L | | 83 ml | | 57.96 ml | |
| Added $H_2O$] | 7.000L | | 715 ml | | 1031 ml | |
| $CH_3OH$ | 7.300L | | | | 2649 ml | |
| Total Solvent | 15.963L | | 798 ml | | 3737.96 ml | |
| Conc. (wt/vol) | 9.87% | | 46.2% | | 1.88% | |

*Based upon addition of following quantities of 37% formaldehyde:
A - 2640 ml;
B - 131.9 ml;
C - 92 ml.
[1]Triton TX100(alkylacyl polyether alcohol).
[2]Carbowax 200(polyethylene glycol, av. mol. wt. 200)

Composition A is a general purpose histological fixative, the manner of utilizing of which is identical with that previously employed with known chemical fixatives. Thus the tissue to be examined is simply imfor election microscopic work is obtained.

According to the second embodiment of this invention, the fixative described herein is employed in a vastly superior method of staining tissue specimens which can be completed in its entirety in a matter of minutes. Specimens so stained demonstrate sufficient permanence, permitting their retention for months without special precautions.

The tissue to be stained is rapidly frozen by any of the well known techniques. The frozen tissue is then sectioned with a conventional microtome and the sections then immersed in a fixing solution described herein. The section has of course already thawed as of this immersion but is fixed in a matter of seconds. A typical period of immersion is five seconds, which surprisingly is sufficient to effect total fixation, and while this period may be extended, no advantages result from a longer immersion.

The section is next immersed in an aqueous solution of hematoxylin. Hematoxylin is a well known stain which chemically is 7,11b-dihydrobenz[b]indeno[1,2-d]pyran-3,4,6a,9,10(6H)-pentol. This step of the process can be conducted in one stage or in two stages. In one embodiment, the section is immersed in the solution of hematoxylin until staining is complete, generally from 10 to 30 seconds. In a second embodiment, the specimen is immersed for a period in a first solution of hematoxylin, removed and rinsed with water and then immersed in a second solution of hematoxylin. In a preferred aspect of this second embodiment, the immersion of the specimen in the second solution of hematoxylin is preceded by a brief immersion in a solution of lithium carbonate which acts in the capacity of an accelerator. Thus for example, the section emerging from the fixing solution is immersed in a first hematoxylin solution for a period of about 15 seconds, rinsed by dipping into water, briefly immersed in a solution of lithium carbonate, say for example for a period of 4 seconds, and again immersed in a solution of hematoxylin for about 5 seconds. At this point, the specimen has fixed and the cell nuclei stained with a bluish-purple hue. The specimen can then be prepared for mounting by washing and drying, the latter being performed in the conventional manner of sequential immersion in progressively more hydrophobic organic media, e.g. 95% ethanol, absolute ethanol and xylol.

If desired, the specimen can also be counterstained using any of the well known differentiating stains, as for example eosin, a fuchsin such as rosaniline, pararosaniline, magenta II, magenta III or acid fuchsin; picric acid or the like.

The hematoxylin can be in any of the usual forms. These include Harris' Hematoxylin, Mayor's Hacmalum, Erlich's Hematoxylin, The alum hematoxylin described by Lie et al., Mayo Clinic Proceedings, 46 319 (May 1971), and the like. One particularly useful preparation is that containing hematoxylin, yellow mercuric oxide and aluminum ammonium sulfate in aqueous glycerin, this reagent generally being known as alum hematoxylin.

EXAMPLE 1

Fixing Solution — Composition A

Four hundred grams of zinc chloride are combined with 120 grams of trichloroacetic acid and 2.64 liters of 37% formaldehyde (corresponding to 1055 grams of 100% formaldehyde) in 7.3 liters of 95% methanol (corresponding to 7 liters of 100% methanol) and 7 liters of water. A slight exothermic reaction occurs and after the solution has reattained room temperature, it is filtered and containerized. This solution, which is ready for use as a tissue fixative, corresponds to a 9.8% wt/vol. solution of trichloroacetic acid, zinc chloride and formaldehyde wherein the weight ratio of zinc chloride to trichloroacetic acid is about 3.33:1 and the weight ratio of formaldehyde to trichloroacetic acid is about 9:1, in aqueous methanol wherein the volume ratio of alkanol to total water (including that added separately, that contained in the 95% methanol and that contained in the 37% formaldehyde) is about 1:1.3. In this composition, volume ratio of alkanol to total water can vary from about 1:1 to about 1:3. A preferred ratio is about 1:1.1 to about 1:1.5. A ratio of zinc chloride to trichloroacetic acid, on a weight basis, can be from about 2:1 to about 4:1. A ratio of 3:1 is highly satisfactory. The ratio of formaldehyde to the trichloroacetic acid can be from about 8:1 to about 10:1, a typical ratio being 9:1. A preferred final concentration for this general purpose fixation is about 10% weight/volume of the trichloroacetic acid, zinc chloride and formaldehyde in the aqueous lower alkanol.

EXAMPLE 2

Fixing Solution — Composition B

Twenty grams of zinc chloride are added to 715 ml of distilled water with agitation. There are next sequentially added 296.5g of trichloroacetic, acid, 131.9 ml of 37% formaldehyde and 0.1 ml of Triton TX-100. The mixture is agitated for 20 minutes and then filtered. The resulting fixative is extremely useful for preparation of bone specimens. The amount of trichloroacetic acid can vary from about 75 to about 85% of the mixture of the three components and that of zinc chloride from about 2 to 8% with the balance being formaldehyde. The water added can vary so that the final concentration of the mixture in the solution is from about 40 to about 50% wt/vol.

EXAMPLE 3

Fixing Solution — Composition C

To a mixture of 2,649.5 ml of methanol and 1031.5 ml of distilled water are added with agitation 11.25g of zinc chloride. There are next sequentially added 22.25g of trichloroacetic acid, 92ml of 37% formaldehyde, 92ml of Carbowax 200 and 0.01 g of methylene blue chloride. The mixture is stirred 20 minutes and filtered.

In this composition, which is advantageous in fixing cytological specimens, the trichloroacetic acid can vary from about 30 to about 40%, by weight of the mixture and the zinc chloride from about 10 to about 20%, by weight with the balance being formaldehyde. The concentration of this mixture in solution will be from about 1 to about 5% wt/vol. The solution can contain from about 1 to about 5%, vol/vol, of the hydrophillic wax. The solvent can vary from about 2:1 to about 3:1 methanol:water.

EXAMPLE 4

Staining Solution (1)

To a solution of 0.67 g of hematoxylin in 33 ml of absolute ethanol are added 33 ml of distilled water, 33 ml of glycerol, 3.3 ml of glacial acetic acid and an excess of potassium aluminum sulfate. The mixture is shaken well and allowed to stand for several weeks after which it is ready for use.

Staining Solution (2)

One gram of hematoxylin, 0.5 g of yellow mercuric oxide and 12 g of aluminum ammonium sulfate are mixed with 140 ml of distilled water. This mixture is boiled for 10 minutes, cooled and adjusted to its original volume with distilled water. Sixty milliliters of glycerin and 8 ml of glacial acetic acid are added and the mixture is then filtered.

Counterstaining Solution

These can be purchased as such and include aqueous solutions of eosin, basic fuchsin, picric acid and the like.

Procedure

Frozen tissue specimens are sectioned on a microtome to a thickness of about $5\mu$. The individual sections are immersed in fixing solution A for approximately 5 seconds and then into staining solution (2) for approximately 15 seconds. After dipping into distilled water for about 3 seconds, the section is immersed in a saturated solution of lithium carbonate for approximately 4 seconds and then immediately reimmersed in staining solution (2) for about 5 seconds. The fixed and stained section is then rinsed in distilled water for 3 seconds and sequentially immersed in 95% ethanol, absolute ethanol, xylol No. 1 and xylol No. 2, each immersion being about 2 seconds, and mounted with a coverslip.

EXAMPLE 5

A counterstained section is obtained according to the procedure of Example 4 by rinsing the specimen with distilled water for 3 seconds following its removal from the second immersion in the staining solution (2), immersing it in 95% ethanol for 2 seconds and then immersing the same in a standard eosin solution for approximately 15 seconds. The thus differentiated section is then sequentially immersed in 95% ethanol, absolute ethanol and xylol as described in Example 4.

What is claimed is:
1. A method of staining tissue for microscopic examination which comprises (a) immersing frozen tissue in an aqueous solution comprising from about 1 to about 50% wt/vol. of a mixture of trichloroacetic acid, zinc chloride and formaldehyde wherein said mixture contains from about 5% to about 85%, by weight of said mixture, of trichloroacetic acid, from about 4% to about 30%, by weight of said mixture, of zinc chloride and from about 3% to about 70%, of by weight of said mixture, of formaldehyde, and (b) thereafter immersing the tissue at least once in an aqueous solution comprising 0.1 to 2% hematoxylin until staining of said tissue is complete.

2. A method of staining tissue for microscopic examination which comprises (a) immersing frozen tissue in an 8 to 20% wt/vol solution of a mixture of trichloroacetic acid, zinc chloride and formaldehyde wherein the weight ratio of zinc chloride to trichloroacetic acid is from about 2:1 to about 4:1 and the weight ratio of formaldehyde to trichloroacetic acid is from about 8:1 to about 10:1, in an aqueous lower alkanol wherein the volume ratio of alkanol to total water is from about 1:1 to about 1:3, and (b) thereafter immersing the tissue at least once in an aqueous solution comprising 0.1 to 2% hematoxylin until staining of said tissue is complete.

3. The method of claim 2 wherein solution (a) is a 9 to 11% solution wt/vol of a mixture of trichloroacetic acid, zinc chloride and formaldehyde wherein the weight ratio of zinc chloride to trichloroacetic acid is from about 3:1 to about 3.5:1 and the weight ratio of formaldehyde to trichloroacetic acid is from about 8:1 to about 10:1, in aqueous methanol wherein the volume ratio of methanol to total water is from 1:1.1 to about 1:1.5.

4. The method of claim 2 wherein said hematoxylin is complexed with alum.

5. The method of claim 2 wherein the immersion of said tissue in said solution of hematoxylin is preceded by immersion of said tissue in a solution of lithium carbonate at least once.

6. The method of claim 2 wherein said tissue is counterstained after immersion in said solution of hematoxylin.

7. The method of claim 6 wherein said counterstain is a eosion.

8. The method of claim 6 wherein said counterstain is a fuchsin.

9. A histological fixative composition comprising a solution of (a) a mixture of from about 5% to about 85%, by weight, of trichloroacetic acid, from about 4% to about 30%, by weight, of zinc chloride, and from about 3% to about 70%, by weight, of 100% formaldehyde, in (b) an aqueous medium, the concentration of said mixture in said solution being from about 1% to about 50%, wt/vol.

10. The composition of claim 9 wherein said aqueous medium is an aqueous alkanol.

11. The composition of claim 10 wherein the alkanol is methanol.

12. The composition of claim 9 wherein said aqueous medium is water.

13. The composition of claim 12 wherein said water contains a surfactant.

14. The composition of claim 9 wherein said mixture contains from about 75% to about 85%, by weight, of trichloroacetic acid, from about 2% to about 8%, by weight, of zinc chloride, and the balance formaldehyde, said mixture being in a 40 to 50%, wt/vol. solution of water containing a surfactant.

15. The composition of claim 14 wherein said mixture contains about 80%, by weight, of trichloroacetic acid, from about 5% to about 6%, by weight, of zinc chloride, and from about 14% to about 15%, by weight of 100% formaldehyde, said mixture being in a 45 to 50%, wt/vol., solution of water, said solution further containing up to 1% vol/vol., of a surfactant.

16. The composition of claim 15 wherein the surfactant is an alkylaryl polyether alcohol.

17. The composition of claim 9 wherein said mixture contains from about 30% to about 40%, by weight, of trichloroacetic acid, from about 10% to about 20%, by weight, of zinc chloride and the balance formaldehyde, said mixture being in a 1 to 5%, wt/vol. solution of aqueous methanol.

18. The composition of claim 17 wherein said solution also contains from 1% to about 5%, vol./vol., of a hydrophillic polyethylene glycol.

19. The composition of claim 18 wherein the ratio of methanol to water is from about 2:1 to about 3:1.

20. The composition of claim 17 wherein said mixture contains about 32%, by weight, trichloroacetic acid, about 16%, by weight, of zinc chloride and about 52%, by weight, of formaldehyde, said mixture being in a 1.5 to 2.5%, wt/vol, solution of aqueous methanol wherein the ratio of methanol to water is from 2.4:1 to 2.5:1.

21. The composition of claim 20 wherein said solution also contains from about 2% to about 3%, vol/vol., of a hydrophillic polyethylene glycol having a molecular weight of about 200.

* * * * *